(12) United States Patent
Bertrand et al.

(10) Patent No.: US 9,302,082 B2
(45) Date of Patent: *Apr. 5, 2016

(54) ADJUSTMENT FOR HYDROCEPHALUS SHUNT VALVE

(71) Applicant: Medtronic Xomed, Inc., Jacksonville, FL (US)

(72) Inventors: William Jeffrey Bertrand, Ventura, CA (US); Robert K. Vaccaro, Ponte Vedra Beach, FL (US); Chun Man Alan Leung, Jacksonville, FL (US); Michael Ayoub, Fribourg (CH); Pierre Jaquier, Avenches (CH); Laetitia Mayor, La Sarraz (CH); Thomas Junker, Solothurn (CH); Guillaume Schmit, Schliern bei Köniz (CH)

(73) Assignee: Medtronic Xomed, Inc., Jacksonville, FL (US)

( * ) Notice: Subject to any disclaimer, the term of this patent is extended or adjusted under 35 U.S.C. 154(b) by 505 days.

This patent is subject to a terminal disclaimer.

(21) Appl. No.: 13/663,807

(22) Filed: Oct. 30, 2012

(65) Prior Publication Data

US 2013/0066253 A1 Mar. 14, 2013

Related U.S. Application Data

(63) Continuation of application No. 13/015,174, filed on Jan. 27, 2011, now Pat. No. 8,298,168.

(51) Int. Cl.
*A61M 27/00* (2006.01)
*F16K 15/18* (2006.01)

(52) U.S. Cl.
CPC ............ *A61M 27/006* (2013.01); *F16K 15/183* (2013.01)

(58) Field of Classification Search
None
See application file for complete search history.

(56) References Cited

U.S. PATENT DOCUMENTS

| 4,127,110 A * | 11/1978 | Bullara .................... 600/561 |
| 4,206,762 A * | 6/1980 | Cosman ................... 600/438 |
| 4,281,666 A * | 8/1981 | Cosman ................... 600/561 |
| 4,354,506 A * | 10/1982 | Sakaguchi et al. ......... 600/561 |
| 4,593,703 A | 6/1986 | Cosman |
| 4,615,691 A * | 10/1986 | Hakim ................ A61F 2/0036 310/181 |
| 4,772,257 A * | 9/1988 | Hakim et al. .................. 604/9 |
| 4,787,886 A * | 11/1988 | Cosman ........................ 604/9 |
| 4,885,002 A * | 12/1989 | Watanabe .......... A61M 27/006 600/561 |
| 5,425,382 A | 6/1995 | Golden et al. |

(Continued)

FOREIGN PATENT DOCUMENTS

| EP | 0735662 B1 | 11/1999 |
| EP | 1512428 A1 | 3/2005 |

(Continued)

OTHER PUBLICATIONS

PCT Search Report for Application No. PCT/US2012/021565, mailed Oct. 22, 2012, 10 pgs.

*Primary Examiner* — Paula L. Craig
(74) *Attorney, Agent, or Firm* — Dicke, Billig & Czaja, PLLC

(57) ABSTRACT

An implantable medical device is disclosed that includes a valve seat and a valve member movable with respect to the valve seat. An adjustment circuit assembly includes a resistive element that is coupled to the valve member and operable to position the valve member relative to the valve seat so as to alter the pressure setting in response to a current applied to the resistive element.

8 Claims, 6 Drawing Sheets

(56) References Cited

U.S. PATENT DOCUMENTS

| | | | |
|---|---|---|---|
| 5,637,083 A | 6/1997 | Bertrand et al. | |
| 5,643,195 A * | 7/1997 | Drevet | A61M 27/006 604/247 |
| 5,704,352 A * | 1/1998 | Tremblay et al. | 600/300 |
| 5,879,297 A | 3/1999 | Haynor et al. | |
| 5,928,182 A * | 7/1999 | Kraus | A61M 27/006 604/9 |
| 6,025,725 A * | 2/2000 | Gershenfeld | H01F 17/0006 324/652 |
| 6,077,299 A * | 6/2000 | Adelberg | A61F 9/00781 604/9 |
| 6,129,668 A | 10/2000 | Haynor et al. | |
| 6,216,028 B1 | 4/2001 | Haynor et al. | |
| 6,278,379 B1 * | 8/2001 | Allen | B60C 23/0408 324/655 |
| 6,326,760 B1 | 12/2001 | Cardoletti et al. | |
| 7,290,454 B2 | 11/2007 | Liu | |
| 7,334,582 B2 | 2/2008 | Bertrand et al. | |
| 7,443,128 B2 | 10/2008 | Bieler et al. | |
| 7,621,878 B2 * | 11/2009 | Ericson et al. | 600/561 |
| 8,241,240 B2 | 8/2012 | Murphy | |
| 8,298,168 B2 * | 10/2012 | Bertrand et al. | 604/9 |
| 8,813,757 B2 * | 8/2014 | Prisco et al. | 128/899 |
| 2002/0022793 A1 | 2/2002 | Bertrand et al. | |
| 2002/0026139 A1 * | 2/2002 | Bertrand et al. | 604/9 |
| 2003/0010949 A1 | 1/2003 | Ito | |
| 2004/0134991 A1 * | 7/2004 | Fletcher | G60K 19/0672 235/491 |
| 2005/0092335 A1 * | 5/2005 | Bertrand et al. | 128/899 |
| 2006/0144155 A1 * | 7/2006 | Liu | 73/753 |
| 2006/0186846 A1 | 8/2006 | Lassen | |
| 2006/0241545 A1 * | 10/2006 | Madsen | A61M 27/006 604/9 |
| 2007/0005000 A1 * | 1/2007 | Ludin | 604/9 |
| 2007/0167867 A1 * | 7/2007 | Wolf | 600/561 |
| 2008/0221436 A1 | 9/2008 | Bertrand et al. | |
| 2009/0005720 A1 | 1/2009 | Ludin et al. | |
| 2009/0105557 A1 * | 4/2009 | Najafi et al. | 600/301 |
| 2009/0112147 A1 * | 4/2009 | Kassem | 604/9 |
| 2009/0143713 A1 * | 6/2009 | Van Dam | A61B 17/11 604/9 |
| 2009/0204019 A1 * | 8/2009 | Ginggen et al. | 600/561 |
| 2010/0022896 A1 * | 1/2010 | Yadav et al. | 600/488 |
| 2010/0241241 A1 * | 9/2010 | McKnight | A61F 2/04 623/23.68 |
| 2011/0112460 A1 * | 5/2011 | Murphy | A61B 5/031 604/9 |
| 2014/0360598 A1 * | 12/2014 | Prisco et al. | 137/487.5 |

FOREIGN PATENT DOCUMENTS

| | | |
|---|---|---|
| EP | 1738792 A1 | 1/2007 |
| EP | 2008683 A1 | 12/2008 |
| JP | 2-211170 | 8/1990 |

* cited by examiner

ADJUSTMENT FOR HYDROCEPHALUS SHUNT VALVE

CROSS-REFERENCE TO RELATED APPLICATIONS

This application is a continuation of U.S. patent application Ser. No. 13/015,174, filed Jan. 27, 2011, now U.S. Pat. No. 8,298,168, and entitled "Adjustment for Hydrocephalus Shunt Valve."

BACKGROUND

1. Technical Field

This disclosure relates generally to surgically implanted physiological shunt systems and related flow control devices. More particularly, the present disclosure relates to a position indicator and adjustment tool for such shunt systems having variable pressure settings for the one-way flow control valves controlling the flow of Cerebral Spinal Fluid (CSF) out of a brain ventricle and preventing backflow of fluid into the brain ventricle.

2. Description of Related Art

A typical adult has a total of about 120-150 cubic centimeters (cc) of CSF with about 40 cc in ventricles in the brain. A typical adult also produces about 400-500 cc/day of CSF, all of which is reabsorbed into the blood stream on a continuous basis.

Sometimes, the brain produces excess CSF or there can be a blockage of the normal CSF pathways and or absorption sites resulting in a condition known as hydrocephalus. Hydrocephalus is a condition of excessive accumulation of CSF in the ventricles or brain tissue. Hydrocephalus can result from genetic conditions, congenital defects infection, cancer, hemorrhage trauma to the brain or as a person ages.

Excessive accumulation of CSF, due to hydrocephalus or other causes, manifests itself as increased pressure within the brain. Whatever the cause, over time, this increased CSF pressure causes damage to the brain tissue. It has been found that relieving the CSF pressure is therapeutically beneficial. This relief is usually performed by draining CSF from the ventricles.

Patients with hydrocephalus normally require, at least over some time period, continuous drainage of excess CSF to maintain normal CSF pressure in the brain. Excessive CSF accumulated in the ventricles of the brain is typically drained away from the brain using a shunt system.

Where hydrocephalus is a chronic condition, the shunt system typically drains the CSF into the patient's peritoneal cavity or into the patient's vascular system. Such shunt systems typically have a catheter implanted in the ventricle of the brain. The catheter is connected to a fluid control device which is in turn connected to a catheter which empties in to the patient's peritoneal cavity or into the patient's vascular system. An example of a fluid control device is shown in U.S. Pat. No. 5,637,083 issued to William J. Bertrand and David A. Watson on Jun. 10, 1997 entitled "Implantable Adjustable Fluid Flow Control Valve", the teaching of which is incorporated herein in its entirety by reference. Current fluid control devices include an inlet connector, an outlet connector and a valve positioned between the inlet connector and the outlet connector. The valve includes a mechanism to control fluid flow through the valve. In some instances, the mechanism includes a magnet embedded within the valve. Rotating a rotor or otherwise shifting of the rotor position changes the internal configuration of the mechanism. Changing the internal configuration of the mechanism produces a variety of pressure or flow characteristics for the valve. As the internal configuration of the valve changes, the pressure or flow characteristics of the valve change.

In use, the valve is subcutaneously placed on the patient's skull. The catheter going to the patient's ventricle is attached to the inlet connector. The catheter going to the patient's peritoneal cavity or vascular system is attached to the outlet connector. In this way, a direction of flow is established from the inlet connector through the valve to the outlet connector. Changing the internal configuration of the mechanism by coupling the external magnet to the internal magnet and rotating the external magnet effects a movement internal to the shunt and produces a variety of pressure or flow characteristics through the valve.

It is desirable to have a number of different settings in order to achieve different pressure and/or flow characteristics of the valve. One complication with current adjustable valves is that once implanted, it is difficult to determine the setting of the valve and/or adjust the setting of the valve. Having more settings for the valve only makes determining and/or adjusting the valve setting more difficult. With some adjustable valves, x-ray images are used to determine the current state or post adjustment state of the valve. By requiring an x-ray, it is time consuming and costly to determine and adjust the valve setting, as well as not being in the best interest of the patient due to x-ray exposure issues.

Another complication with current adjustable valves is compatibility with magnetic resonance imaging (MRI) procedures. As many current adjustable valves utilize magnets for adjusting and/or determining a valve setting, their function can be disrupted due to interaction of magnetic components in the valve with the applied magnetic field created during the MRI procedure. In particular, the valve setting can be altered to a random, undesirable setting. If the valve setting is not returned to the desired setting after the MRI procedure, this situation can be extremely harmful to a patient. As such, the valve setting needs to be immediately reset to the desired setting upon conclusion of the MRI procedure. In any event, improvement of valves for the treatment of hydrocephalus can provide great benefit.

SUMMARY

Concepts presented herein relate to determining and/or adjusting a pressure setting for an implantable medical device. In one embodiment, the device includes a valve seat and a valve member interfacing with the valve seat to establish a pressure setting indicative of a pressure where fluid will flow through the valve seat. An adjustment circuit assembly includes a resistive element that is coupled to the valve member and operable to adjust force on the valve member relative to the valve seat so as to alter the pressure setting in response to a current applied to the resistive element.

In another aspect, an implantable flow control device includes a valve defining a plurality of pressure settings. A connector assembly is coupled to the valve and movable with respect to the valve to adjust a pressure setting for the valve. An adjustment circuit assembly includes a setting coil, adjustment capacitor and resistive element electrically connected to one another. The resistive element is coupled to the connector assembly. A reading circuit assembly includes an antenna coil, a reading capacitor and a sensing coil electrically connected to one another. The reading circuit assembly also includes a moveable member coupled to the connector assembly and moveable with respect to the sensing coil. Current induced in the setting coil causes the resistive element to move the connector assembly relative to the valve. Current induced at the proper frequency in the antenna coil generates a signal indicative of the pressure setting.

In another aspect, a method of controlling flow of fluid in an implantable device includes providing a valve in the device adjustable to a plurality of pressure settings. An oscillating electromagnetic field resonant with an adjustment circuit assembly coupled with the valve is received. Current is induced in a resistive element of the adjustment circuit assembly and a pressure setting of the device is adjusted based on the current in the resistive element.

In yet a further aspect, a method of operating an implantable flow device includes providing a valve adjustable to a plurality of pressure settings and coupling a connector assembly to the valve. The connector assembly is movable with respect to the valve to adjust a pressure setting for the valve. A reading circuit assembly is further provided that includes an antenna coil, a sensing coil and a member movable with respect to the sensing coil. The member is connected to the connector assembly such that a resonant frequency of the reading circuit assembly is altered as a function of a position of the connector assembly with respect to the valve.

DETAILED DESCRIPTION

Figure 1:
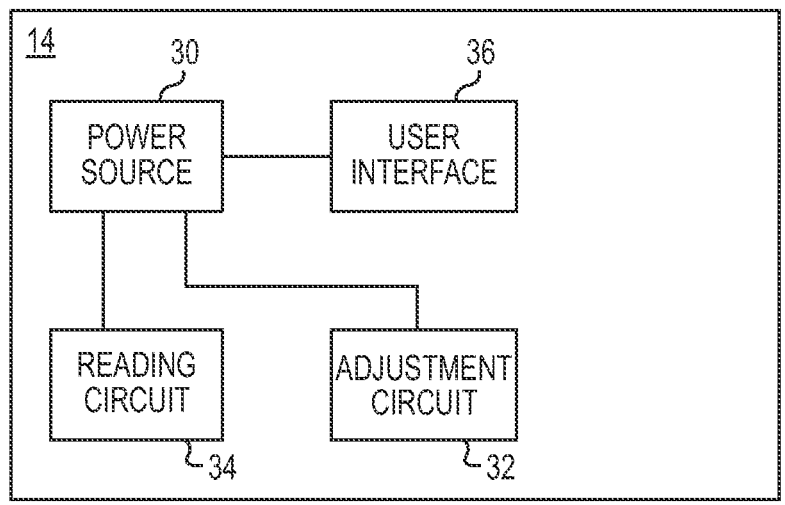
FIG. 1 is a schematic block diagram of an adjustable shunt system.
Figure 1:
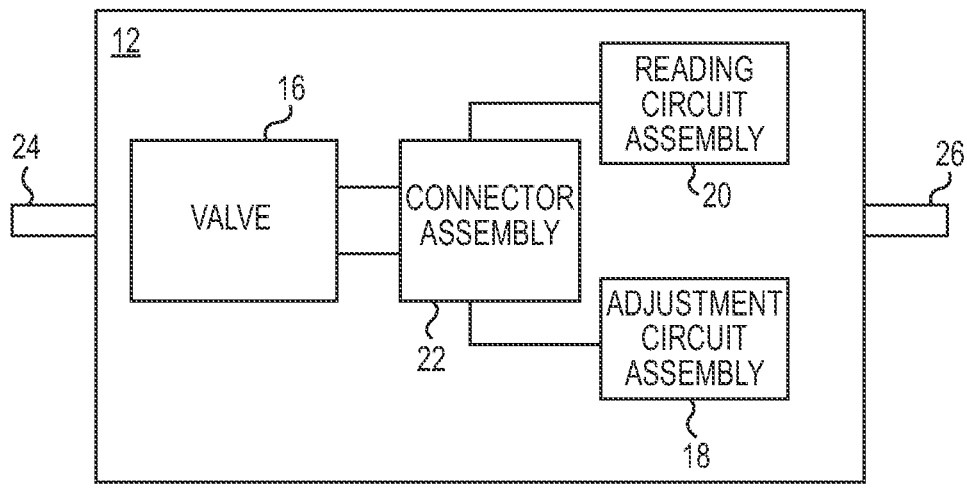

FIG. 1 is a schematic block diagram of an adjustable shunt system 10 including an implantable flow control device 12 (e.g., a shunt) and an electronic valve reader and adjustment tool 14. In general, device 12 can be implanted in a patient to regulate flow of fluids (e.g., CSF discussed above) within the patient based on a pressure setting (also known as a valve setting) for the device 12. Tool 14, in turn, can be a handheld mechanism configured to subcutaneously read and adjust the pressure setting of the device 12 when positioned proximate thereto. As such, tool 14 is a non-contact device capable of reading and adjusting device 12 while being located outside the body of a patient. In particular, the tool 14 can create an oscillating electromagnetic field that is received by device 12. The field can cause device 12 to adjust the pressure setting and provide feedback indicative of a pressure setting as will be discussed below.

The device 12 includes a valve 16, an adjustment circuit assembly 18, a reading circuit assembly 20 and a connector assembly 22 coupling the valve 16 with the adjustment circuit assembly 18 and the reading circuit assembly 20. Fluid is allowed to flow through the valve 16 from an inlet connector 24 to an outlet connector 26 depending on a valve setting indicative of a cracking pressure (when valve 16 is embodied as a check valve) for valve 16. The adjustment circuit assembly 18 defines a number of settings to alter pressure and/or flow characteristics of fluid through device 12. Adjustment circuit assembly 18 is coupled to valve 16 through connector assembly 22 to alter the pressure setting based on signals (e.g., an electromagnetic field) from tool 14. Reading circuit 20 is also coupled to valve 16 through connector assembly 22 and configured to provide a signal indicative of the pressure setting to tool 14 in response to a signal (e.g., an electromagnetic field) from tool 14. Device 12 can be formed of biocompatible materials in order to be subcutaneously positioned within a patient. Additionally, the materials can limit the use of magnetic materials such that a pressure setting for device 12 will not be altered during an MRI procedure.

Tool 14 includes a power source 30 configured to provide power to an adjustment interface 32, a reading interface 34 and a user interface 36. An exemplary tool is further described in co-pending U.S. patent application Ser. No. 13/015,195, filed on Jan. 27, 2011, entitled "Reading and Adjusting Tool for Hydrocephalus Shunt Valve", the contents of which are hereby incorporated by reference in their entirety. Adjustment interface 32 of tool 14 is adapted to provide signals (e.g., an electromagnetic field) to adjustment circuit assembly 18 within device 12. In particular, the adjustment interface 32 can send signals that match a resonant frequency of the adjustment circuit assembly 18 in order to induce a current therein. This current is used to adjust the pressure setting for valve 16. In one embodiment the resonant frequency of adjustment circuit assembly 18 is approximately 100 kHz, although other frequencies can be used.

In a similar manner, reading interface 34 is adapted to send a signal (e.g., an electromagnetic field) to reading circuit assembly 20 that matches a resonant frequency of the reading circuit assembly 20. However, the resonant frequency of reading circuit assembly 20 changes as a function of the pressure setting for valve 16. As a result, reading interface 34 is configured to transmit signals for multiple frequencies (e.g., by performing a scanning operation) and determine which frequency is the resonant frequency for reading circuit assembly 20. In particular, when the frequency of the signal sent by reading interface 34 matches the resonant frequency of reading circuit assembly 20, current will be induced within the reading circuit assembly 20, creating a magnetic field that can be sensed by reading interface 34. In one embodiment, the resonant frequency of reading circuit assembly 20 is around 1 MHz, adjustable within a range of frequencies capable of generation by reading interface 34. Using the resonant frequency information, the pressure setting of valve 16 can be determined, for example using a lookup table. User interface 36 can provide a visual indication of operation for adjustment interface 32 and reading interface 34, allow input to the tool 14 and provide a visual indication of proximity of the tool 14 to device 12. For example, user interface 36 can include a screen to display pressure information, one or more buttons to alter operation of tool 14 and/or a set of indicators.

Figure 2:
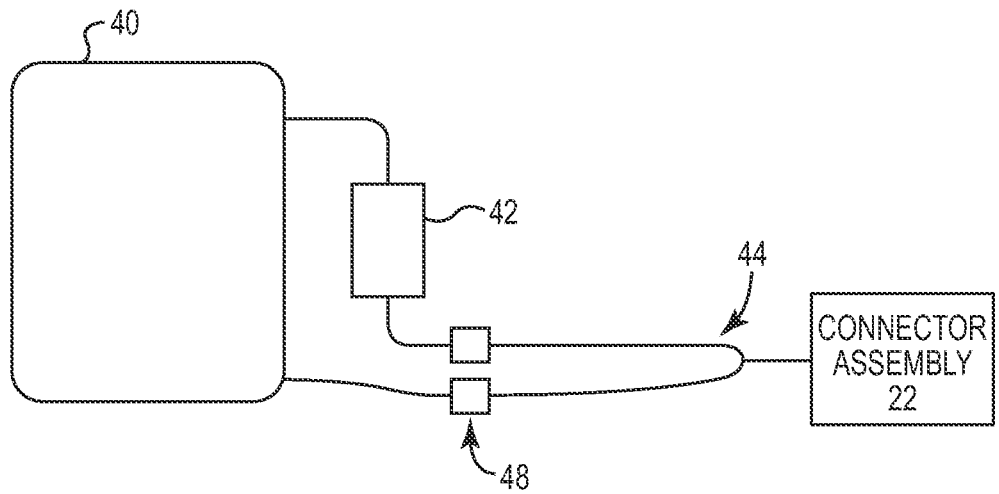
FIG. 2 is a schematic block diagram of an adjustment circuit assembly positioned in a flow control device.

FIG. 2 is a schematic view of adjustment circuit assembly 18 positioned within device 12, including a setting coil 40, an adjustment capacitor 42, a resistive element 44 (herein embodied as a wire) and a crimping structure 48. As discussed above, in one embodiment, adjustment circuit assembly 18 is a series resonant circuit configured to resonate at a particular frequency based on signals received from tool 14 (e.g., from adjustment interface 32). Signals from tool 14 that match the resonant frequency of adjustment circuit assembly 18 will create a current in coil 40, which will then pass through capacitor 42 and element 44.

As electricity flows through adjustment circuit assembly 18, element 44 is heated resistively, resulting in a mechanical movement of the element 44 acting against crimping structure 48. In particular, element 44 is made of a suitable shape memory alloy (SMA), which is heated resistively when a current is induced in coil 40. Although herein embodied as a wire, element 44 can take other forms such as a flat stock. As can be appreciated, shape memory alloys return to a specific shape and/or size through a temperature dependent phase change. Element 44 is configured to contract upon reaching a transition temperature to a contracted state and thus provide a mechanical movement for which to alter a valve setting for valve 16. Upon cooling, element 44 then returns to an expanded state. Crimping structure 48 holds element 44 in place at both ends of the element 44, which forms a loop opposite the crimping structure. In alternative embodiments, element 44 need not form a loop and can be coupled to connector assembly 22 in various different manners. In one embodiment, the element 44 is formed of nickel titanium (nitinol) and has a transition temperature of around 70 degrees Celsius. Upon reaching the transition temperature, element 44 contracts a predetermined length, which in one embodiment is around 2.5% of an overall length of the element 44. When element 44 is coupled to connector assembly 22, this contraction then triggers movement of connector assembly 22 in order to alter a pressure setting for the valve 16. As illustrated in FIG. 2, element 44 forms a loop at an end opposite crimping structure 48. This loop can be coupled to the connector assembly 22 so as to translate mechanical movement thereto upon contraction of the element 44. As contraction of element 44 (rather than utilization of a magnetic mechanism) serves as the trigger to adjust the pressure setting for valve 16, inadvertent adjustment of the pressure setting for valve 16 can be avoided during an MRI procedure.

Figure 3:
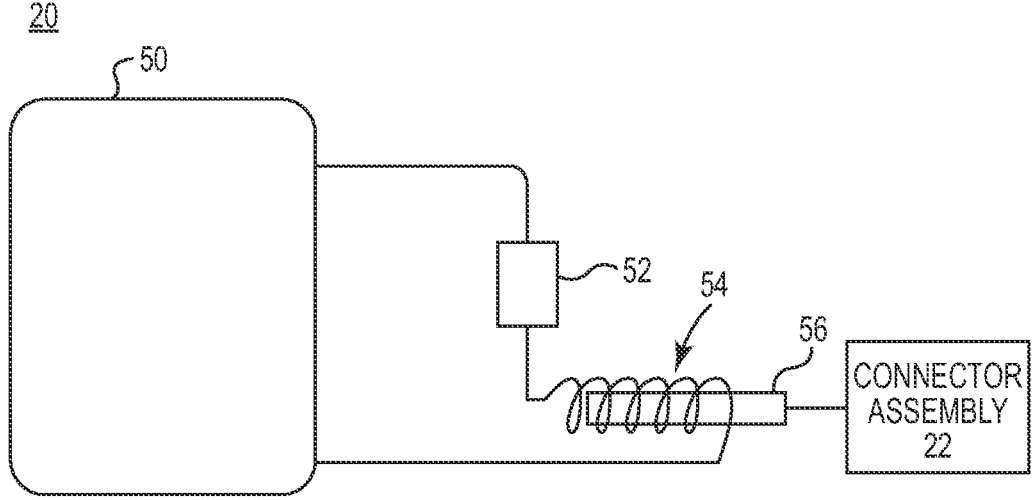
FIG. 3 is a schematic block diagram of a reading circuit assembly positioned in a flow control device.

FIG. 3 is a schematic diagram of reading circuit assembly 20 within device 12. Reading circuit assembly 20 includes an antenna coil 50, a reading capacitor 52, a sensing coil 54 and a moveable member 56. Moveable member 56 is coupled to connector assembly 22 and, in one embodiment, is connected in fixed relation thereto. Similar to adjustment circuit assembly 18, reading circuit assembly 20 can be a series resonant circuit in which signals provided by reading interface 34 of tool 14 are received by antenna coil 50. Signals received from tool 14 that match the resonant frequency of circuit 20 will energize antenna coil 50, causing electricity to be transmitted through capacitor 52 and sensing coil 54. In an alternative embodiment, antenna coil 50 can be eliminated such that a resonant frequency of capacitor 52 sensing coil 54 is matched by tool 14. Movable member 56 can be formed of a material that changes the resonant frequency of circuit 20 as the movable member 56 moves relative to sensing coil 54. In one example, moveable member 56 is formed of a ferrite and is cylindrically shaped. The ferrite alters inductance of sensing coil 54, depending on how much of the ferrite material is positioned within the sensing coil 54. In another embodiment, the movable member 56 can be "E" shaped such that a middle portion is positioned within an interior of sensing coil 54 while upper and lower arms of the member 56 are positioned outside sensing coil 54. In any event, reading interface 34 senses a magnetic field created by electricity passing through circuit 20, which is indicative of a pressure setting for device 12.

In alternative embodiments, adjustment circuit assembly 18 and reading circuit assembly 20 can be modified in various configurations. For example, in one embodiment, setting coil 40 and antenna coil 50 can be combined into a single coil. The preferred or this combined circuit can further be implemented with diodes, if desired. In other embodiments, capacitors 42 and/or 52 can be eliminated.

Figure 4:
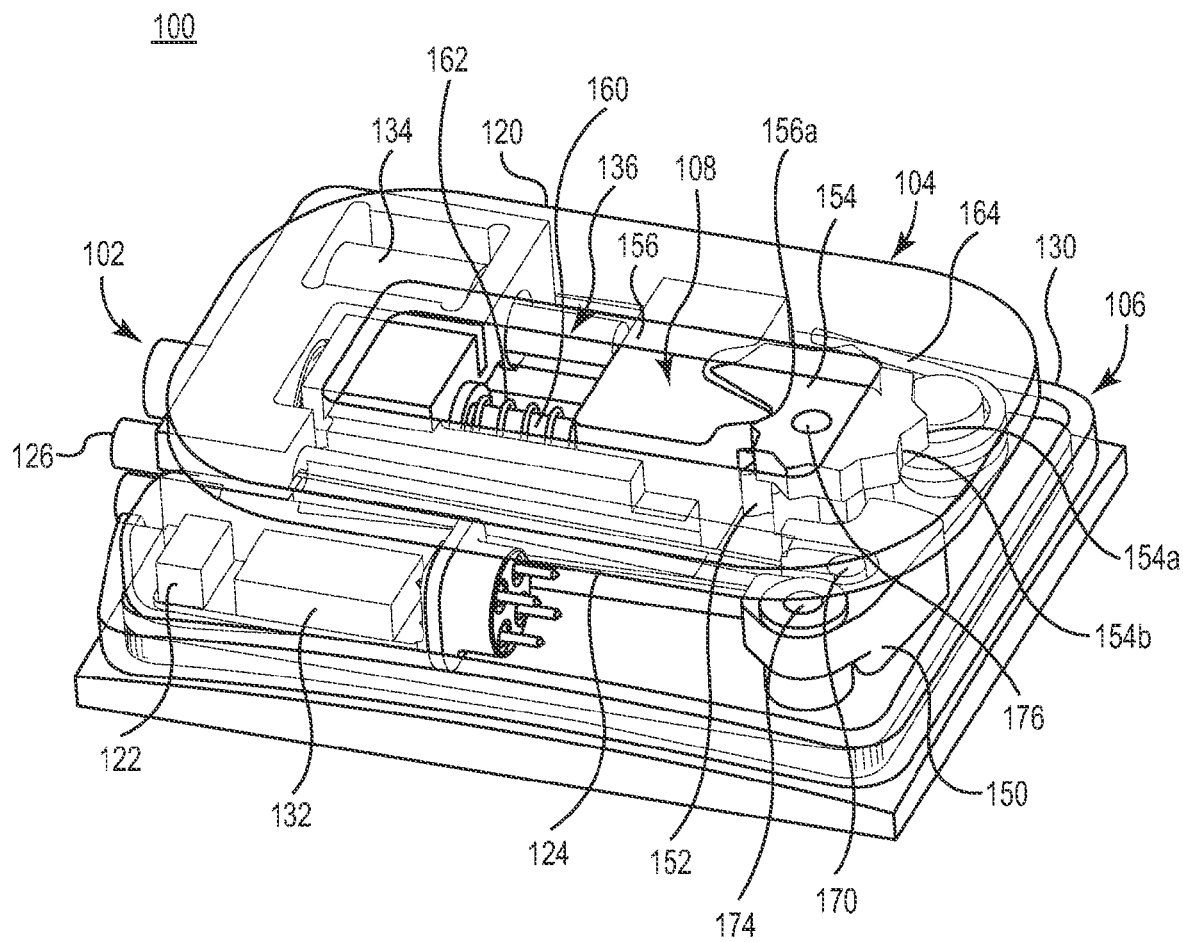
FIG. 4 is a perspective view of a first embodiment of a flow control device.
Figure 5:
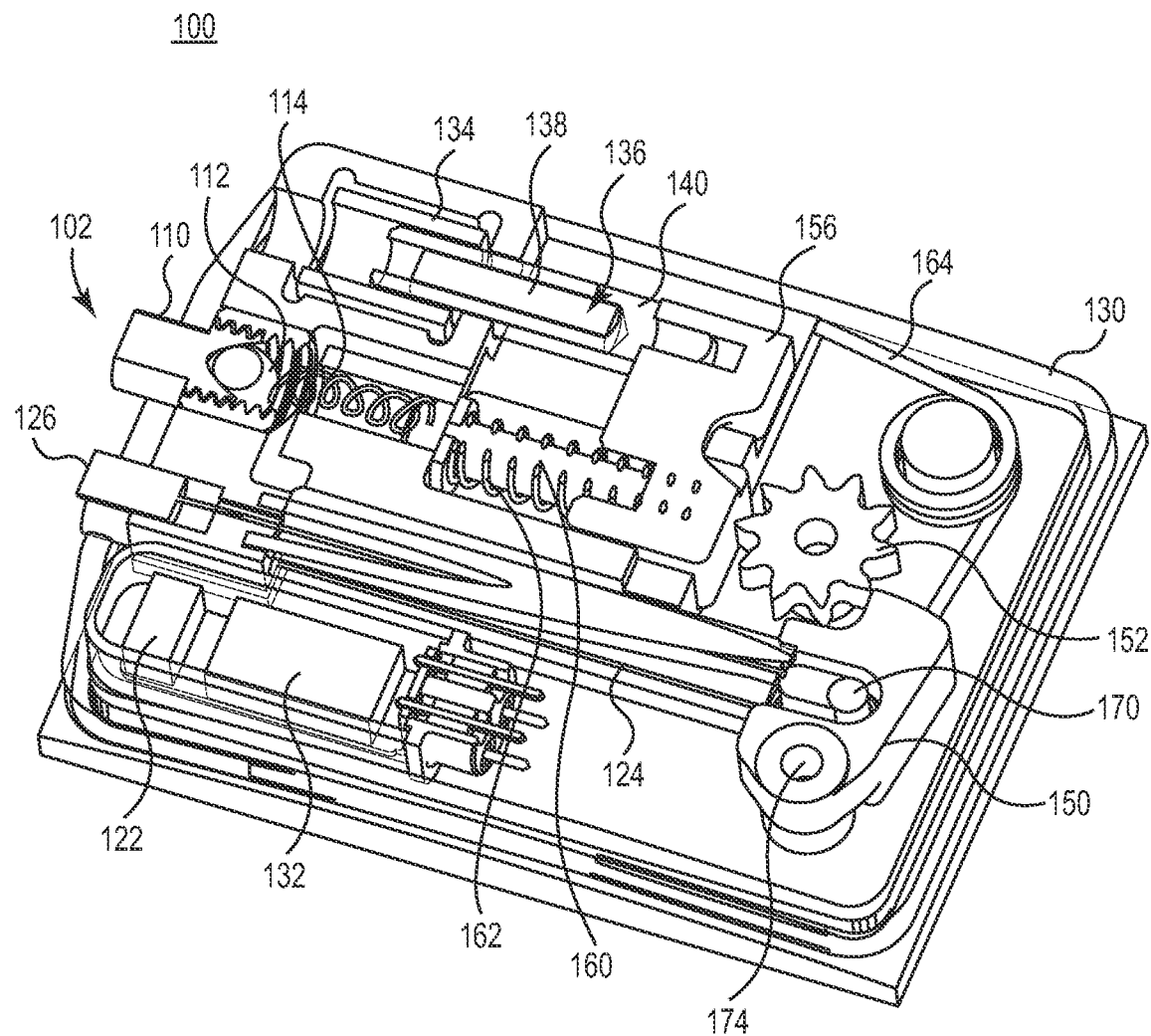
FIG. 5 is a cross-sectional view of the flow control device illustrated in FIG. 4.

FIGS. 4 and 5 illustrate a device 100 that is operable as a hydrocephalus flow control device (e.g., as device 12 in FIG. 1). Device 100 includes a valve 102, an adjustment circuit assembly 104, a reading circuit assembly 106 and a connector assembly 108. Details of these components of device 100 are provided below. In general, connector assembly 108 is directly coupled to valve 102 in order to provide a particular cracking pressure for device 100, as a function of a position of connector assembly 108 relative to valve 102. In turn, adjustment circuit assembly 104 and reading circuit assembly 106 are coupled to connector assembly 108 in order to adjust a position of connector assembly 108 and transmit a signal indicative of a position of the connector assembly 108, respectively.

In the illustrated embodiment, valve 102 is operable as an adjustable check valve and includes a valve seat 110 and a corresponding valve member 112 moveable with respect to the valve seat 110. A valve spring 114 urges valve member 112 against valve seat 110, creating a cracking pressure for valve 102. In general, valve spring 114 is coupled to connector assembly 108 and alters pressure (i.e., force) placed on valve member 112 as a function of the position of connector assembly 108. As fluid pressure builds within valve 102, valve member 112 is urged away from valve seat 110. When the fluid pressure is at a level to overcome the pressure that valve spring 114 places on valve member 112 against valve seat 110, fluid will flow through valve 102. Valve 102 can take other forms in alternative embodiments. For example, valve spring 114 (herein illustrated as a helical compression spring) can be embodied as a flat spring wherein a position where force applied to the spring is laterally displaced from the valve member 112, either directly or through use of a fulcrum positioned between the valve member and the position where force is applied to the spring. Although not illustrated herein, valve 102 can include other features as desired such as a reservoir, siphon control device, etc.

Adjustment circuit assembly 104 is coupled to valve 102 through connector assembly 108 to alter a pressure setting of valve 102 and includes a setting coil 120, an adjustment capacitor 122, a resistive element 124 and a crimping structure 126. Adjustment circuit assembly 104 operates in a similar manner to adjustment circuit assembly 18 discussed above. When positioned proximate device 100, tool 14 (FIG. 1) can operate to energize setting coil 120, thus inducing a current therein, which then passes through capacitor 122 and resistive element 124. As current passes through element 124, the element 124 is heated, ultimately causing contraction of element 124 acting against crimping structure 126, which remains stationary as element 124 contracts. In one embodiment, element 124 is insulated so as to prevent adjacent components from overheating and/or becoming subject to electrical current passing therethrough. As discussed below, element 124 is coupled to connector assembly 108 at an end opposite crimping structure 126 such that contraction of element 124 causes movement of connector assembly 108 to adjust a pressure setting for device 100.

Reading circuit assembly 106 is configured to provide a signal indicative of the connector assembly 108 relative to valve 102 and includes an antenna coil 130, a reading capacitor 132, a sensing coil 134 and a moveable member 136. In the embodiment illustrated, moveable member 136 includes a ferrite core 138 surrounded by a support member 140, directly coupled to connector assembly 108. Reading circuit assembly 106 operates in a similar manner to reading circuit assembly 20 discussed above. When positioned proximate device 100, tool 14 can operate to energize antenna coil 130, thus inducing current therein, which then passes through capacitor 132 and sensing coil 134. Movable member 136 and in particular ferrite core 138, moves to various positions with respect to sensing coil 134, which ultimately alters a resonant frequency for reading circuit assembly 106. Inducement of current in reading circuit assembly 106 generates a signal indicative of the pressure setting. The tool 14 can sense a magnetic field generated by reading circuit assembly 106 to provide an indication for the pressure setting of device 100.

Connector assembly 108 includes a ratchet arm 150, a gear 152, a cam 154, a cam follower 156, a push rod 160, a return spring 162 and a ratchet spring 164. As discussed in more detail below, ratchet arm 150 engages teeth of gear 152 to provide a rotational force thereto. Cam 154 is rotationally fixed to gear 152 and includes teeth extending at varying distances to engage cam follower 156. The teeth place varying displacements on the cam follower 156, thus adjusting a position of cam follower 156 in relation to valve 102. As such, an amount of force placed on the valve member 112 relative to the valve seat 110 is adjusted. Depending on the position of cam follower 156, more or less pressure is exerted on valve spring 114 by push rod 160. Return spring 162 operates to bias cam follower 156 against cam 154. Additionally, ratchet spring 164 operates to reset ratchet arm 150 after providing rotational force to gear 152. In an alternative embodiment, ratchet arm 150 can be replaced by a suitable escapement arm, including separate index and drive pawls to rotate gear 152. In yet a further embodiment, ratchet arm 150 can be a linear ratchet movable in a linear direction (rather than rotationally) to adjust a pressure setting. Moreover, cam 154 can be an axial cam that includes a plurality of steps with variable axial displacements to engage a cam follower and adjust force placed on valve spring 114.

Valve 102 is coupled to connector assembly 108 through push rod 160, and in particular push rod 160 is configured to push against valve spring 114. Adjustment circuit assembly 104 is coupled to connector assembly 108 through ratchet arm 150. As illustrated, element 124 of adjustment circuit assembly 104 is directly coupled to ratchet arm 150. Cam follower 156 of connector assembly 108 is directly coupled to moveable member 136 of the reading circuit assembly 106. As such, movable member 136 moves with cam follower 156 and with respect to sensing coil 134.

During adjustment of a pressure setting for device 100, setting coil 120 is energized as discussed above such that electricity passes through resistive element 124. When element 124 reaches a transition temperature due to resistance created therein, element 124 contracts, acting against crimping structure 126. At an end opposite crimping structure 126, element 124 is coupled to ratchet arm 150 through a connecting pin 170. When element 124 contracts, a force is applied to pin 170, causing ratchet arm 150 to rotate about a pivot 174. In turn, rotation of ratchet arm 150 causes rotation of gear 152.

Gear 152 is rotationally fixed to cam 154, causing cam 154 to rotate with gear 152. Cam 154 includes a variable radius about its rotational axis 176. In particular, cam 154 includes a plurality of teeth that extend from rotational axis 176 at different lengths. In an alternative embodiment, cam 154 can be smooth. Each tooth includes a peak (e.g., peak 154a), with valleys (e.g., valley 154b) positioned on either side of the peak. The plurality of teeth engage cam follower 156 and, depending on a rotational position of cam 154, pushes cam follower 156 toward valve 102. In particular, contraction of element 124 to a contracted state causes cam 154 to rotate a predetermined distance such that cam follower 156, and in particular a cam follower peak 156a, engages a peak of a corresponding tooth on cam 154. Once element 124 cools and returns to its expanded state, cam follower 156 moves to a valley immediately adjacent the peak on cam 154. Thus, cam 154 undergoes a two-step rotation, one step when element 124 is heated and contracts (causing cam follower 156 to engage a tooth peak) and one step when wire 124 cools and expands (causing cam follower 156 to engage a tooth valley). As such, element 124 indexes the valve 102.

As cam follower 156 is pushed toward valve 102, push rod 160 engages valve spring 114 and pushes valve member 112 against valve seat 110. Depending on a position for cam follower 156, more or less pressure is pressure is provided on valve member 112, ultimately controlling an amount of fluid that passes through valve 102. As cam follower 156 moves with respect to valve 102, movable member 136 moves with respect to sensing coil 134. As movable member 136 moves with respect to sensing coil 134, the resonant frequency for reading circuit assembly 106 changes. As a result, the resonant of frequency is indicative of a pressure setting for device 100.

Figure 6:
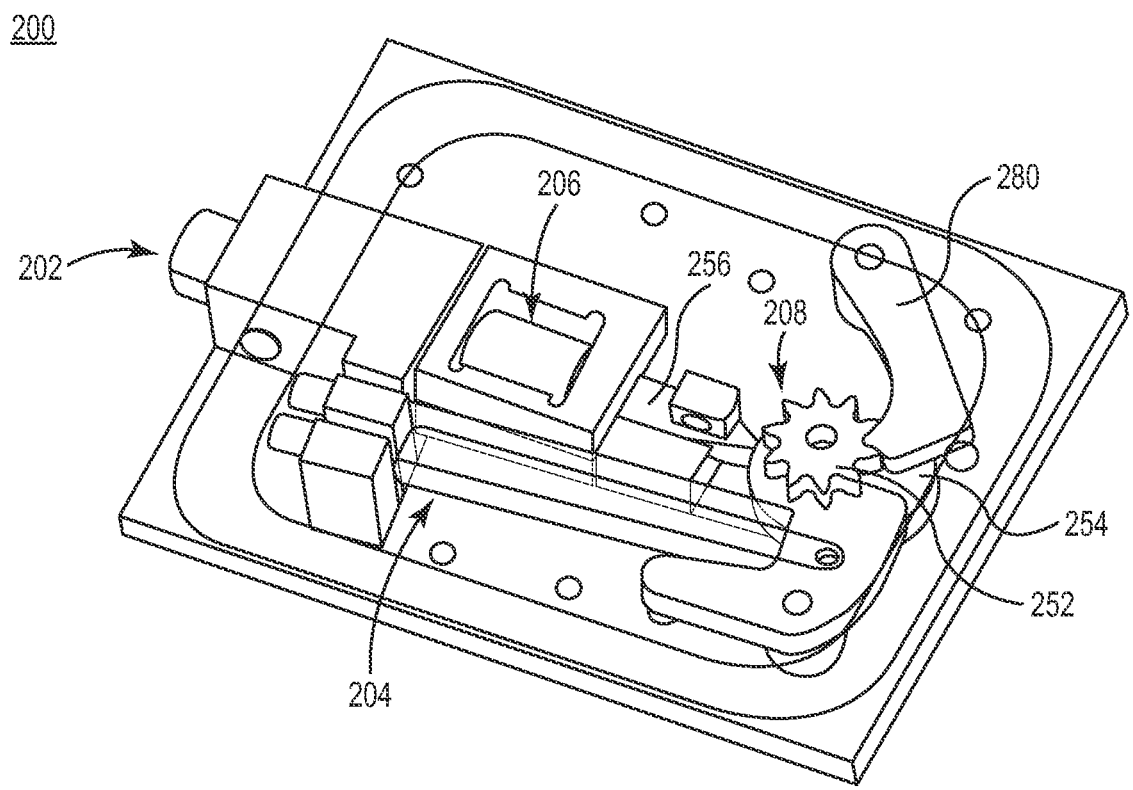
FIG. 6 is a perspective view of a second embodiment of a flow control device.
Figure 7:
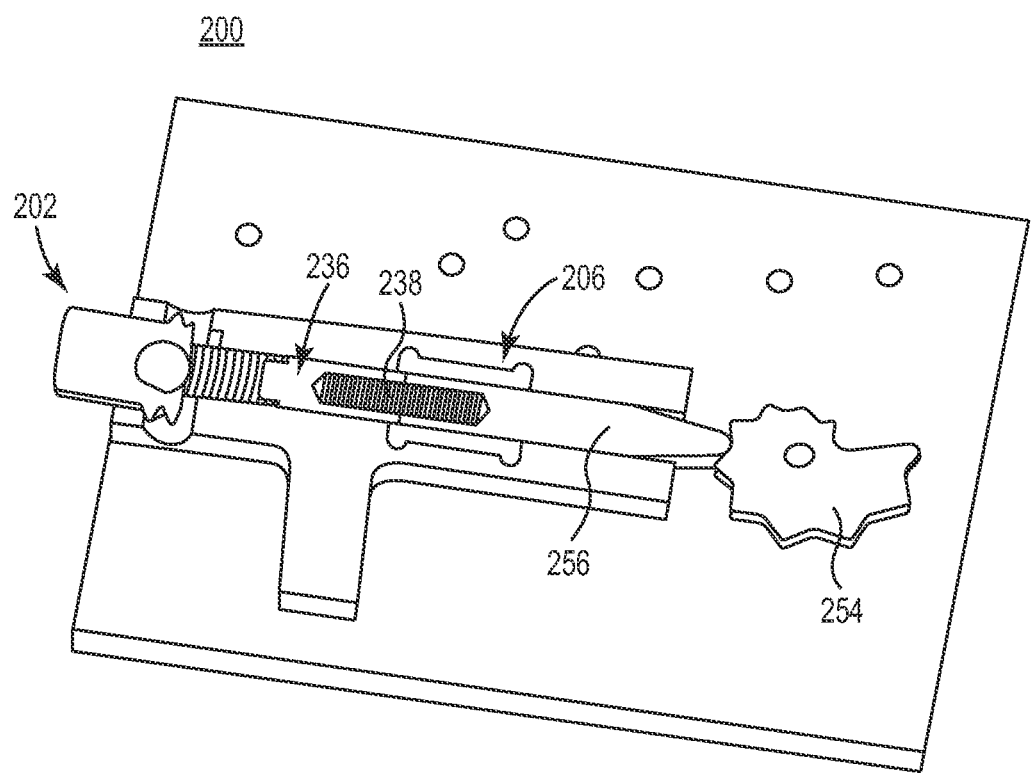
FIG. 7 is a cross-sectional view of the flow control device of FIG. 6.

FIGS. 6 and 7 illustrate an alternative embodiment of a flow control device 200. Device 200 operates in a similar manner to device 100 in FIGS. 4 and 5. Device 200 includes valve 202, an adjustment circuit assembly 204, a reading circuit assembly 206 and a connector assembly 208. In general, these elements operate similar to corresponding elements as discussed with respect to FIGS. 4 and 5 above. For sake of brevity, several elements are not illustrated or discussed. Workers skilled in the art will appreciate that similar structure from device 100 can be incorporated into device 200. In the embodiment illustrated, however, cam follower 256 is in-line with the movable member 236 and corresponding ferrite core 238. Moreover, the gear 252 is located on top of cam 254 and a detent arm 280 is provided to engage teeth in the gear 252.

Although the present disclosure has been described with reference to preferred embodiments, workers skilled in the art will recognize that changes can be made in form and detail without departing from the spirit and scope of the present disclosure.

What is claimed is:

1. An adjustable shunt system, comprising:
    an implantable flow control device, comprising:
        a valve seat;
        a valve member interfacing with the seat to establish a pressure setting indicative of a pressure where fluid will flow through the valve seat;
        an adjustment circuit assembly including a resistive element coupled to the valve member and operable to adjust force on the valve member relative to the valve seat so as to alter the pressure setting in response to a current applied to the resistive element; and
        a reading circuit assembly including an antenna coil, a sensing coil and a member movable with respect to the sensing coil, the member configured to alter a resonant frequency of the reading circuit assembly as a function of a position of the member with respect to the sensing coil; and
    a tool, comprising:
        an adjustment circuit operably couplable with the adjustment circuit assembly so as to generate an oscillating electromagnetic field so as to induce a current in the resistive element; and
        a reading circuit operatively couplable with the reading circuit assembly and configured to induce a current in the antenna coil to generate a signal indicative of the pressure setting.

2. The system of claim h wherein the adjustment circuit assembly further includes a setting coil electrically connected to the resistive element.

3. The system of claim 2, wherein the adjustment circuit assembly further includes a capacitor electrically connected to the setting coil and resistive element.

4. The system of claim 1, wherein the reading circuit assembly further includes a capacitor electrically connected to the antenna coil and the sensing coil.

5. The system of claim 1, wherein the adjustment circuit is configured to generate signals at a first frequency and the reading circuit is configured to generate signals at a second frequency different than the first frequency.

6. The system of claim 1, wherein the reading circuit is configured to scan a signal across a range of frequencies in order to generate a signal in the antenna coil indicative of the pressure setting.

7. The system of claim 1, wherein the adjustment circuit generates a signal having a frequency of approximately 100 kilohertz.

8. The system of claim 1, wherein the reading circuit generates a signal having a frequency of approximately 1 megahertz.

* * * * *